United States Patent [19]

Ikeda et al.

[11] Patent Number: 5,387,727
[45] Date of Patent: Feb. 7, 1995

[54] METHOD OF PRODUCING PENTAFLUOROPHENYL ALKALI METAL SALT USING PENTAFLUOROBENZENE IN A CHAIN ETHER TYPE SOLVENT

[75] Inventors: Yoshihiko Ikeda, Shinnanyo; Takeo Yamane, Yamaguchi; Eiichi Kaji, Shinnanyo; Kenji Ishimaru, Shinnanyo, all of Japan

[73] Assignee: Tosoh Akzo Corporation, Tokyo, Japan

[21] Appl. No.: 168,210

[22] Filed: Dec. 17, 1993

[30] Foreign Application Priority Data

Dec. 28, 1992 [JP] Japan ................................. 4-361481

[51] Int. Cl.$^6$ ............................................. C07C 25/13
[52] U.S. Cl. ..................................... 570/143; 570/123; 570/190
[58] Field of Search ................. 570/143, 123, 144, 190

[56] References Cited

U.S. PATENT DOCUMENTS 3,269,928  8/1966  Haszeldine .......................... 570/143

FOREIGN PATENT DOCUMENTS 996498   6/1965  United Kingdom ................. 570/143
1016275  5/1983  U.S.S.R. ............................. 570/143

*Primary Examiner*—Werren B. Lone
*Attorney, Agent, or Firm*—Oblon, Spivak, McClelland, Maier & Neustadt

[57] ABSTRACT

Disclosed is a production method of generating pentafluorophenyl alkali metal salt represented by a general formula $C_6F_5M$ (M denotes an alkali metal ion) by reacting pentafluorobenzene represented by $C_6HF_5$ with an organometallic compound represented by a general formula RM (R denotes a hydrocarbon group of $1 \sim 10$ carbon number which may contain a functional group having no influence on the reaction.

2 Claims, No Drawings

METHOD OF PRODUCING PENTAFLUOROPHENYL ALKALI METAL SALT USING PENTAFLUOROBENZENE IN A CHAIN ETHER TYPE SOLVENT

BACKGROUND OF THE INVENTION

The present invention relates to a method for producing pentafluorophenyl alkali metal salt with good efficiency using pentafluorobenzene as a raw material therefor.

The pentafluorophenyl alkali metal salt obtainable according to the invention is used as an important reacting agent for introducing pentafluorophenyl group into boron in case it is reacted with boron compounds, for example, boron trichloride etc. to produce boron derivatives which are very useful as co-catalyst ingredients for polymerization reaction, for example, tris(pentafluorophenyl)borane (For example, Synthesis of Fluoroorganic Compounds. p. 190, Springer-Verlag (1985)).

Up to now, several synthetic reactions for pentafluorophenyl alkali metal salt are known. For example, a method of producing pentafluorophenyllithium through bromine-metal exchange reaction using relatively expensive bromopentafluorobenzene as a starting raw material for a source of pentafluorophenyl group and butyllithium is already known. For example, in Synthesis of Fluoroorganic Compounds, p. 190, Springer-Verlag (1985), pentafluorophenyllithium is prepared in diethylether-hexane at −70° C. and is reacted with sulfur dioxide to give lithium pentafluorophenylsulfenate with 94% yield. Also, a method of producing pentafluorophenyllithium through hydrogen-metal exchange reaction using pentafluorobenzene as a starting raw material for a source of pentafluorophenyl group and butyllithium is already known. For example, in J. Org. Chem., 29, 2385 (1964), pentafluorophenyllithium prepared from pentafluorobenzene and butyllithium is reacted with carbon dioxide gas to give pentafluorobenzoic acid wherein the reaction yield is unknown, but the purification yield, depending on reaction solvent system, is 68% in diethylether-hexane system, 80.9% in diethylether type and 82% in diethylether-tetrahydrofuran system respectively.

Further, in J. Org. Chem., 31, 4229, (1966), pentafluorophenyllithium prepared from pentafluorobenzene and butyllithium is reacted with hexafluoroacetone to give undecafluoro-2-phenyl-2-propanol wherein the reaction yield is unknown, but the purification yield is 79%.

Bromopentafluorobenzene has higher reactivity with organometallic compounds such as butyllithium over pentafluorobenzene. When producing pentafluorophenyllithium through hydrogen-metal exchange reaction using butyllithium, the reaction completes for 5 minutes or so in either a chain ether type solvents such as diethyl ether or a cyclic ether type solvents such as tetrahydrofuran to give pentafluorophenyllithium nearly quantitatively. However, since bromopentafluorobenzene is obtained by brominating pentafluorobenzene, it becomes expensive. Eventually a use of more inexpensive pentafluorobenzene would be desired industrially.

However, since pentafluorobenzene is less reactive than bromopentafluorobenzene, when producing pentafluorophenyllithium through deprotonation reaction using butyllithium, it is reported in J. Org. Chem., 29, 2385, (1964) that the yield is more increased in a chain ether type solvent to which a cyclic ether type solvent such as tetrahydrofuran is added than in a chain ether type solvent alone.

In general, it is known that organometallic compounds such as butyllithium react with ether type solvent at a temperature higher than 0° C. Hence, the organometallic compounds such as butyllithium are usually dealt commercially as their solutions in saturated hydrocarbon type solvents such as hexane, cyclohexane, pentane and others. Hence, when producing pentafluorophenyllithium from pentafluorobenzene in chain ether type solvent using butyllithium solution in the saturated hydrocarbon type solvent such as hexane, which is dealt commercially, the saturated hydrocarbon type solvent which is a diluting solvent for butyllithium is mixed into the reaction system to afford a mixed solvent of a chain ether type solvent with a hydrocarbon type solvent, making the reaction further difficult to take place (J. Org. Chem., 29, 2385, ( 1964)).

On the other hand, when producing a compound having very strong Lewis acidity, for example tris(pentafluorophenyl)borane etc., cyclic ether type solvent, it exists in the reaction system, leads to form a complex that the cyclic ether is coordinated in the product by its strong coordinating power, which becomes difficult to be removed therefrom in many cases.

In view of said situation, the inventors have studied various production methods wherein, using pentafluorobenzene as a starting raw material for the source of pentafluorophenyl group in a reaction solvent of not using cyclic ether type solvent such as tetrahydrofuran, pentafluorophenyl alkali metal salt can be produced with good reproductivity in high yield, and, as the result, have reached the present invention.

SUMMARY OF THE INVENTION

The gist of the present invention concerns a method of producing pentafluorophenyl alkali metal salt represented by a formula [III]

$$C_6F_5M \qquad [III]$$

(wherein M denotes an alkali metal ion) by reacting 0.5∼1.5 equivalents of an organometallic compound represented by a formula [II]

$$RM \qquad [II]$$

(wherein M denotes an alkali metal ion and R denotes a hydrocarbon group having 1∼10 carbon number which may contain a functional group having no influence on the reaction) with 1 equivalent of pentafluorobenzene represented by a formula [I]

$$C_6HF_5 \qquad [I]$$

in an ether type solvent, a hydrocarbon type solvent or a mixed solvent of the ether type solvent and the hydrocarbon type solvent at a temperature of −120° C.∼80° C.

DETAILED DESCRIPTION OF THE INVENTION

In following, the invention will be illustrated in detail.

The chain ether type solvents referred to so in the invention indicate diethyl ether, dipropyl ether, diisopropyl ether, dibutyl ether, diisoamyl ether, 1,2-dimethoxyethane, 1,2-diethoxyethane, di-2-methoxyethyl ether, etc.

The cyclic ether type solvents referred to so in the invention indicate tetrahydrofuran, tetrahydropyran, 1,4-dioxane etc.

Next, the hydrocarbon type solvents referred to so in the invention indicate saturated hydrocarbons such as pentane, isopentane, hexane, cyclohexane, heptane, octane, nonane, decane, undecane, dodecane, tridecane, tetradecane, pentadecane, hexadecane, n-paraffin or petroleum ether etc. and aromatic hydrocarbons such as benzene, toluene, o-xylene, m-xylene, p-xylene, 1,2,3-trimethylbenzene, 1,2,4-trimethylbenzene, 1,2,5-trimethylbenzene, 1,3,5-trimethylbenzene, ethylbenzene, propylbenzene or butylbenzene etc., and a mixture thereof.

Next, the functional groups having no influence on the reaction in the formula [II] referred to so in the invention indicate methyl group, ethyl group, propyl group, isopropyl group, propenyl group, 2-isopropenyl group, allyl group, butyl group, sec-butyl group, tert-butyl group, isobutyl group, pentyl group, sec-pentyl group, tert-pentyl group, neo-pentyl group, isopentyl group, hexyl group, sec-hexyl group, isohexyl group, sec-isohexyl group, cyclohexyl group, phenyl group, benzyl group, o-tolyl group, m-tolyl group, p-tolyl group, methoxymethyl group, methylthiomethyl group, 2-dimethylaminoethyl group, o-anisyl group, m-anisyl group, p-anisyl group, trimethylsilylmethyl group, etc., and examples of or organometallic compounds represented by the formula II include methyllithium, ethyllithium, propyllithium, isopropyllithium, butyllithium, isobutyllithium, sec-butyllithium, tert-butyllithium, pentyllithium, isopentyllithium, sec-pentyllithium, tert-pentyllithium, sec-isopentyllithium, hexyllithium, iso-hexyllithium, sec-hexyllithium, cyclohexyllithium, phenyllithium, o-tolyllithium, m-tolyllithium, p-tolyllithium, trimethylsilylmethyllithium, phenylsodium, o-tolylsodium, m-tolylsodium, p-tolylsodium, butyllithium/potassium-tert-butoxide or butyllithium/sodium-tert-butoxide etc. and preferably, isopropyllithium, sec-butyllithium, tert-butyllithium, sec-pentyllithium, tert-pentyllithium, sec-isopentyllithium, sec-hexyllithium, cyclohexyllithium, butyllithium/potassium-tert-butoxide or butyllithium/sodium-tert-butoxide etc. which are strong in basicity.

The invention will be illustrated below successively with concrete production methods.

When 0.5~1.5 equivalents of the organometallic compound represented by the formula [II] is reacted with 1 equivalent of pentafluorobenzene of a solution in which pentafluorobenzene represented by the formula [I] is dissolved in an ether type solvent, a hydrocarbon type solvent or a mixed solvent of the ether type solvent and the hydrocarbon solvent at a temperature of $-120°$ C.~$-80°$ C. to generate pentafluorophenyl alkali metal salt represented by the formula [III], a lot of unreacted pentafluorobenzene come to remain if organometallic compound represented by the formula [II] is too less than pentafluorobenzene represented by the formula [I], while there is a fear of the halogen-metal exchange reaction with also fluorine of produced pentafluorophenyl alkali metal salt represented by the formula [III] if excess amount of organometallic compound is used. Therefore, it is preferable to employ 0.8~1.20 equivalents of organometallic compound represented by the formula [II]. If the reaction temperature is too lower than $-80°$ C., the reaction proceeds extremely slowly, while if it is too higher than 0° C., side reactions proceed extremely rapidly, thus coming to very low yield in both cases. Hence, it is desirable to conduct the reaction in a range of $-80°$ C.~$0°$ C. The reaction mixture is kept under the reaction at the same temperature for 5~120 minutes, and then pentafluorophenyl alkali metal salt is prepared.

Pentafluorophenyl alkali metal salt produced herein is $C_6F_5Li$, $C_6F_5N^a$ or $C_6F_5K$.

In following, the invention will be illustrated in more detail using the examples, but these are examples for the concrete illustration and the invention undergoes no restriction by the examples below. The yield of reaction is a value obtained by quantitatively determining pentafluorotoluene produced by reacting with a large excess amount of methyl iodide by means of gas chromatography, by quantitatively determining pentafluorobenzoic acid produced by blowing carbon dioxide by means of gas chromatography, or by quantitatively determining N,N-dimethylanilinium tetrakis(pentafluorophenyl)borate produced by corresponding cation exchange with aqueous N,N-dimethylanilinium chloride after reacting with 0.25 equivalents of boron trichloride by means of $^{19}F$-NMR.

EXAMPLE 1

Inside of a 100 ml volume glass three-neck flask equipped with a 50 ml volume glass dropping funnel, temperature resistor and septum rubber was sufficiently replaced with nitrogen. Into the flask, 5 g (29.8 mmol) of pentafluorobenzene and 30 ml of diethyl ether were charged, of which solution was cooled to $-65°$ C. Thereafter, 12.3 g (29.8 mmol) of 15.5 wt. % pentane solution of tert-butyllithium charged into the dropping funnel were added dropwise while making the inner temperature not to exceed $-55°$ C. After the completion of dropwise addition, the reaction mixture was kept at a temperature of $-65°$~$-55°$ C. with stirring to give pentafluorophenyllithium.

The solution of pentafluorophenyllithium produced was added to a tetrahydrofuran solution of methyl iodide at a temperature of $-55°$~$-65°$ C., kept at the same temperature for 30 minutes with stirring, then the temperature was slowly elevated up to the room temperature, and pentafluorotoluene was quantitatively determined by means of gas chromatography to give 97.1% yield.

EXAMPLE 2

Inside of a 100 ml volume glass three-neck flask equipped with a 50 mol volume glass dropping funnel, temperature resistor and septum rubber was sufficiently replaced with nitrogen. Into the flask, 5 g (29.8 mmol) of pentafluorobenzene and 30 ml of diethyl ether were charged, of which solution was cooled to $-65°$ C. Thereafter, 14.2 g (34.3 mmol) of 15.5 wt. % hexane solution of sec-butyllithium charged into the dropping funnel were added dropwise while making the inner temperature not to exceed $-55°$ C. After the completion of dropwise addition, the reaction mixture was kept at a temperature of $-65°$~$-55°$ C. with stirring to give pentafluorophenyllithium. The yield of pentafluorobenzoic acid obtained by blowing of carbon dioxide into the prepared solution of pentafluorophenyllithium was 96.8% by means of gas chromatographic quantitative determination.

EXAMPLE 3

Inside of a 100 ml volume glass three-neck flask equipped with a 50 ml volume glass dropping funnel, temperature resistor and septum rubber was sufficiently replaced with nitrogen. Into the flask, 5 g (29.8 mmol) of pentafluorobenzene and 30 ml of diethyl ether were charged, of which solution was cooled to −65° C. Thereafter, 12.3 g (29.8 mmol) of 16.1 wt. % hexane solution of sec-butyllithium charged into the dropping funnel were added dropwise while making the inner temperature not to exceed −55° C. After the completion of dropwise addition, the reaction mixture was kept at a temperature of −65°∼−55° C. with stirring to give pentafluorophenyllithium. The yield of pentafluorobenzoic acid obtained by blowing of carbon dioxide into the prepared solution of pentafluorophenyllithium was 96.8% by means of gas chromatographic quantitative determination.

EXAMPLE 4

Inside of a 100 ml volume glass three-neck flask equipped with a 50 ml volume glass dropping funnel, temperature resistor and septum rubber was sufficiently replaced with nitrogen. Into the flask, 5 g (29.8 mmol) of pentafluorobenzene and 30 ml of diethyl ether were charged, of which solution was cooled to −65° C. Thereafter, 12.3 (29.8 mmol) of 16.1 wt. % pentane solution of tert-butyllithium charged into the dropping funnel were added dropwise while making the inner temperature not to exceed −55° C. After the completion of dropwise addition, the reaction mixture was kept at a temperature of −65°∼−55° C. with stirring to give pentafluorophenyllithium. To the prepared solution of pentafluorophenyllithium was added 1 mol/L hexane solution (7.45 mL, 7.45 mmol) of boron trihalide at a temperature of −65°∼−55° C., kept for 30 minutes at the same temperature with stirring and then the temperature was elevated up to the room temperature to afford a solution of lithium tetrakis(pentafluorophenyl)borate, which was subjected to quantitative determination employing pentafluorotoluene as an inner standard by means of $^{19}$FNMR. The yield was 92.3%.

EXAMPLE 5

Inside of a 100 ml volume glass three-neck flask equipped with a 50 ml volume glass dropping funnel, temperature resistor and septum rubber was sufficiently replaced with nitrogen. Into the flask, 15.5 g (29.8 mmol) hexane solution of 15.5 wt. % butyllithium, 3.3 g (29.8 mmol) potassium tertbutoxide and 15 ml diethyl ether were charged, of which solution was cooled to −65° C. Thereafter, 5 g (29.8 mmol) pentafluorobenzene and 15 ml diethyl ether charged into the dropping funnel were added dropwise while making the inner temperature not to exceed −55° C. After the completion of dropwise addition, the reaction mixture was kept at a temperature of −65°∼−55° C. with stirring to give pentafluorophenyllithium.

The prepared solution of pentafluorophenyllithium was added to a tetrahydrofuran solution of methyl iodide at a temperature of −55°∼−65° C., kept at the same temperature for 30 minutes and then the temperature was slowly elevated, pentafluorotoluene of which was subjected to quantitative determination to give 95.9% yield.

EXAMPLE 6

Inside of a 100 ml volume glass three-neck flask equipped with a 50 ml volume glass dropping funnel, temperature resistor and septum rubber was sufficiently replaced with nitrogen. Into the flask, 5 g (29.8 mmol) of pentafluorobenzene and 30 ml of diethyl ether were charged, of which solution was cooled to −65° C.

Thereafter 15.9 g (29.8 mmol) of 15.0 wt. % hexane solution of butylsodium charged into the dropping funnel was added dropwise while making the inner temperature not to exceed −55° C. After the completion of dropwise addition, the reaction mixture was kept at a temperature of −65°∼−55° C. with stirring to give pentafluorophenylsodium. The prepared solution of pentafluorophenylsodium was added to tetrahydrofuran solution of methyl iodide at a temperature of −55°∼−65° C., kept at the same temperature for 30 minutes with stirring and the temperature was slowly elevated, of which pentafluorotoluene was subjected to quantitative determination by means of gas chromatography to give 93.2% yield.

The invention relates to an auxiliary catalyst when preparing a catalyst for cation complex polymerization.

The invention is valuable in the point of capable of providing a method of producing pentafluorophenyl alkali metal salt being an important reaction reagent for the production of compounds, for example, tris(pentafluorophenyl)borane etc. with high yield in a chain ether type solvent, not from pentafluorobromoenzene, but from pentafluorobenzene which is of lower price.

What is claimed is:

1. A method for producing a pentafluorophenyl alkali metal salt of formula (III):

$$C_6F_5M \qquad (III)$$

wherein M denotes an alkali metal ion, comprising:
reacting from 0.5 to 1.5 equivalents of an organometallic compound of formula (II):

$$RM \qquad (II)$$

wherein M denotes an alkali metal ion and R denotes a hydrocarbon group having 1 to 10 carbon atoms which may contain a functional group having no influence on the reaction, with one equivalent of pentafluorobenzene represented by formula (I):

$$C_6HF_5$$

in a solvent selected from the group consisting of an ether solvent, a hydrocarbon solvent and a mixture of an ether solvent and a hydrocarbon solvent at,a temperature of −120° C. to 80° C.

2. A method of claim 1, wherein the reaction is conducted in a chain ether solvent.

* * * * *